United States Patent
Huang

(10) Patent No.: US 6,371,639 B1
(45) Date of Patent: Apr. 16, 2002

(54) PROBE COVER OF A TYMPANIC THERMOMETER AND METHOD FOR MANUFACTURING THE SAME

(75) Inventor: Yu Chien Huang, Hsinchu (TW)

(73) Assignee: Radiant Innovation Inc., Hsinchu (TW)

( * ) Notice: Subject to any disclaimer, the term of this patent is extended or adjusted under 35 U.S.C. 154(b) by 0 days.

(21) Appl. No.: 09/687,954

(22) Filed: Oct. 13, 2000

(51) Int. Cl.[7] .............................. G01K 1/08; A61B 5/00; A61B 6/00; A61B 1/227
(52) U.S. Cl. ........................ 374/158; 600/474; 600/549; 264/161; 264/322
(58) Field of Search ................................ 374/158, 209; 264/161, 322; 600/474, 549, 184, 185, 200, 203; 206/306, 305; 29/557

(56) References Cited

U.S. PATENT DOCUMENTS

| | | | | |
|---|---|---|---|---|
| 3,719,396 A | * | 3/1973 | VanDeWalker et al. | 406/74 |
| 5,088,834 A | * | 2/1992 | Howe et al. | 374/158 |
| 5,163,418 A | * | 11/1992 | Fraden et al. | 374/158 |
| 5,179,936 A | * | 1/1993 | O'Hara et al. | 374/158 |
| 5,271,407 A | * | 12/1993 | Pompei et al. | 374/158 |
| RE34,599 E | * | 5/1994 | Suszynski et al. | 374/158 |
| 5,609,564 A | * | 3/1997 | Makita et al. | 600/200 |
| 5,833,367 A | * | 11/1998 | Cheslock et al. | 374/158 |
| 6,022,140 A | * | 2/2000 | Fraden et al. | 374/158 |
| 6,156,148 A | * | 12/2000 | Beerwerth et al. | 600/474 |
| 6,254,271 B1 | * | 7/2001 | Lin | 374/158 |

\* cited by examiner

*Primary Examiner*—Diego Gutierrez
*Assistant Examiner*—Stanley J. Pruchnic, Jr.
(74) *Attorney, Agent, or Firm*—Pro-Techtor International Services

(57) ABSTRACT

A probe cover of a tympanic thermometer and method for manufacturing the same are provided in the invention. The method for manufacturing the probe cover includes: (a) forming an infrared transparent sheet; (b) forming a sheath having a closed end and a circumferential peripheral flange, a plurality of unwanted parts being formed on an outer circumferential wall between the circumferential peripheral flange and the closed end of the sheath, and the closed end being formed into a flat window; (c) hot-pressing the plurality of unwanted parts to form a plurality of fins; (d) removing the plurality of fins to form a plurality of cutting marks; (e) turning over the sheath to make the plurality of cutting marks located inside the sheath so that the outer circumferential wall thereof is smooth; and (f) combining the circumferential peripheral flange of the probe cover with a ring base.

7 Claims, 2 Drawing Sheets

PROBE COVER OF A TYMPANIC THERMOMETER AND METHOD FOR MANUFACTURING THE SAME

BACKGROUND OF THE INVENTION

1. Field of the Invention

The present invention relates generally to a probe cover, and more particularly, to a probe cover of a tympanic thermometer.

2. Description of the Related Art

Clinical thermometers are very helpful in the diagnosis of diseases. The tympanic membrane is generally considered by the medical community to be superior to oral, rectal, or underarm sites for representing the body's core temperature. The temperature of the tympanic membrane can be measured by detecting the infrared radiation from the tympanic membrane in the ear canal. In addition, the time needed for the body temperature measuring by using an infrared thermometer is short. The use of infrared thermometers therefore has become more and more prevalent.

To measure the infrared emission in the external ear canal, the probe of a tympanic thermometer has to be inserted into the external ear canal for sensing the infrared emission from the tympanic membrane for determining the temperature of the tympanic membrane. However, a tympanic thermometer that is used to determine the body temperature of different patients can cause contamination and infections. To prevent this disadvantage, the probe of a tympanic thermometer can be provided with a probe cover that is disposable after use.

Referring to FIG. 1, a probe cover of a tympanic thermometer disclosed in U.S. Pat. No. 5,163,418 to Fraden et al. includes a sheath 31 and ring-shaped base 32. The sheath 31 is formed from an infrared transparent film having a thickness of 0.001 inch. The closed end of the sheath 31 is flat and acts as a window 311 for infrared emission. The circumferential wall 312 includes a plurality of pleats. The circumferential peripheral flange is attached to the ring-type base 32. The base 32 is designed to fit tightly on the probe of the thermometer. When the base 32 is fitted on the probe of the thermometer, the window 311 contacts with the front inlet of the probe. The drawback of the probe cover lies in that when it is inserted in the ear canal, the pleats on the wall 312 of the sheath 31 scrape the skin of the canal and cause a patient to feel uncomfortable. In addition, the sheath generates noises when it is pressed. Moreover, wrinkles appear on the window 311 when the probe cover is fitted on the probe and cause stray radiation that adversely affects the accuracy of the measured temperature.

Referring to FIG. 2, a probe cover of a tympanic thermometer disclosed in U.S. Pat. No. 5,088,834 to Howe et al. includes a frustum-shaped sheath 41 and a base 42 formed from a single piece of infrared transparent material. The dimensions of the sheath 41 are chosen to let it fit on the probe closely. The thickness of the sheath 41 is gradually less from the proximal portion to the distal portion such that the window 411 has the minimal thickness of approximately 0.001 to 0.0005 inch. The base 42 circumferentially engages with the open end (proximal end) of the sheath 41 to secure the sheath 41 on the probe of the thermometer. This type of sheath has no pleats and is comfortable for use. However, its disadvantage lies in that the sheath is formed by plastically deforming the material from its proximal open end to its distal closed end. The material is plastically deformed in a significant length so that the maximum thickness change of the material is from 0.03 to 0.0005 inch and this causes difficulty in the quality control during the manufacturing process.

SUMMARY OF THE INVENTION

It is therefore an object of the invention to provide a probe cover of a tympanic thermometer and method of manufacturing the same in order to make the manufacturing easy and make the user feel comfortable.

To achieve the above-mentioned objective, a probe cover of a tympanic thermometer and method for manufacturing the same are provided. The method for manufacturing the probe cover includes: (a) forming an infrared transparent sheet; (b) forming a sheath having a closed end and a circumferential peripheral flange, a plurality of unwanted parts being formed on an outer circumferential wall between the circumferential peripheral flange and the closed end of the sheath, and the closed end being formed into a flat window; (c) hot-pressing the plurality of unwanted parts to form a plurality of fins; (d) removing the plurality of fins to form a plurality of cutting marks; (e) turning over the sheath to make the plurality of cutting marks located inside the sheath so that the outer circumferential wall thereof is smooth; and (f) combining the circumferential peripheral flange of the probe cover with a ring base.

BRIEF DESCRIPTION OF THE DRAWINGS

The above and other objects and the features and effects of the present invention can be best understood by referring to the following detailed description of the preferred embodiment and the accompanying drawings, wherein.

DETAILED DESCRIPTION OF THE INVENTION

Figure 2:
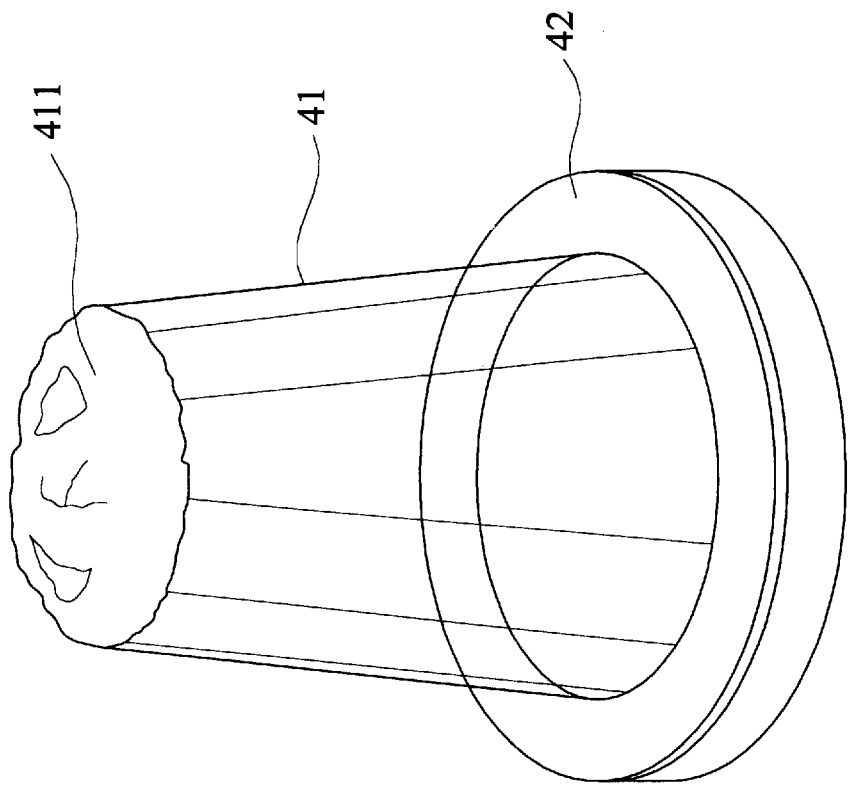
FIG. 2 is a pictorial view showing a probe cover for an infrared thermometer disclosed in U.S. Pat. No. 5,088,834.
Figure 1:
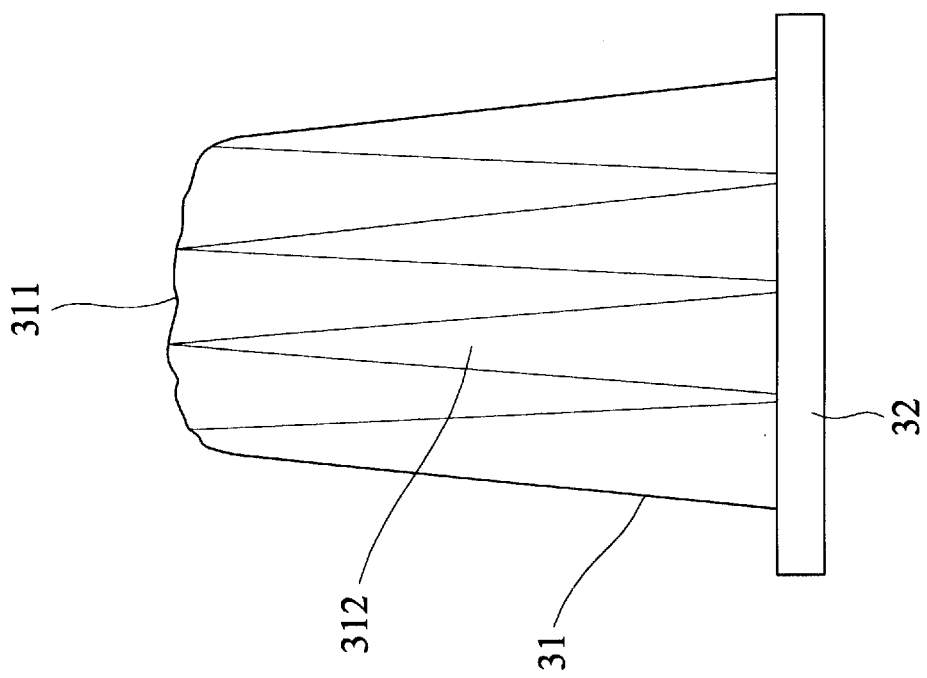
FIG. 1 is an elevational view showing a probe cover for an infrared thermometer disclosed in U.S. Pat. No. 5,163,418.
Figure 3:
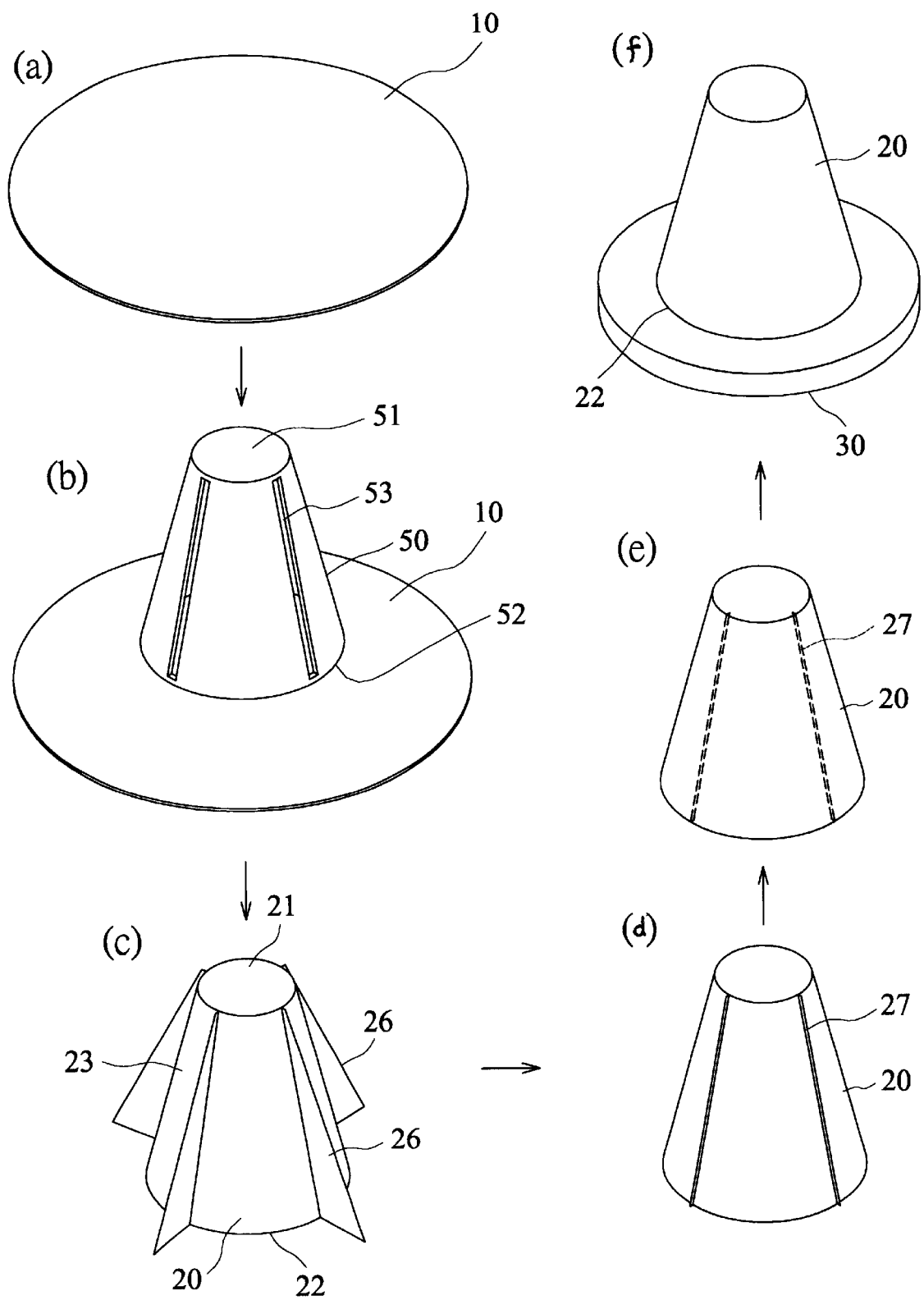
FIG. 3 is a schematic illustration showing the method for manufacturing the probe cover in accordance with the preferred embodiment of the invention.

Referring to FIG. 3, the method for manufacturing the probe cover of the invention will be described in the following.

(a) First, an infrared transparent sheet 10, which is a circular sheet having a thickness of about 0.001 inch and a diameter of about 8 cm, is formed.

(b) Next, a sheath 20 having a closed end 21 and a circumferential peripheral flange 22 is formed by using a forming member 50 having the same shape as that of a probing portion of the tympanic thermometer. The forming member 50 includes a closed end 51 and a circumferential peripheral flange 52. The closed end 51 is formed into a plane. Four slots 53 are formed on the outer circumferential wall between the circumferential peripheral flange 52 and the closed end 51. The cross-sectional area of the forming member 50 gradually decreases from the circumferential peripheral flange 52 to the closed end 51. In this process, the forming member 50 is placed on the sheet 10, and then, the sheet 10 is pressed into the forming member 50 so that it is covered by the forming member 50. Thereafter by upwardly applying high-pressure air onto the bottom of the sheet 10, the sheet 10 having the same shape as that of the forming member 50 is formed. That is, a sheath 20 having a closed end 21 and a circumferential peripheral flange 22 is formed. The closed end 21 is formed into a flat window. The cross-sectional area of the sheath 20 gradually decreases from the circumferential peripheral flange 22 to the closed end 21. When forming the sheath 20, the redundant material of the sheet 10 is blown out of the slots 53 of the forming member 50 by the high-pressure air. Therefore, four unwanted parts (not shown) are uniformly formed on the outer circumferential wall 23 of the sheath 20 from the circumferential peripheral flange 22 to the closed end 21.

(c) Subsequently, the four unwanted parts are hot-pressed into four fins 26. That is, four fins 26 are uniformly formed on the outer circumferential wall 23 of the sheath 20.

(d) Then, the four fins 26 are cut out and four cutting marks 27 are formed at the same time.

(e) Next, the sheath 20 is turned over so that the four cutting marks 27 are located inside the sheath 20. At this time, the sheath 20 has a smooth outer surface or outer circumferential wall.

(f) Finally, the circumferential peripheral flange 22 of the sheath 20 is combined with a ring base 30 by a method of, for example, hot pressing.

From the description of the above-mentioned embodiment, it is easily understood that the portion of the sheet 10 forming the closed end 21 and the outer circumferential wall 23 is not plastically deformed when forming the sheath 20 having a shape corresponding to the probing portion of the tympanic thermometer of the invention. Thus, the thickness of the sheet keeps unchanged, and it is easily controlled in manufacturing. Additionally, since the cutting marks 27 are located inside the sheath 20 and the sheath 20 has a smooth outer surface, a user does not feel uncomfortable resulting from the scraping on the ear canal by the pleats.

Furthermore, if the cutting technology is so precise that remaining cutting marks 27 are quite insignificant, the step (e) can be omitted. In this case, the insignificant cutting marks 27 will not make the user's ear canal feel uncomfortable.

While the invention has been described by way of example and in terms of a preferred embodiment, it is to be understood that the invention is not limited to the disclosed embodiment. To the contrary, it is intended to cover various modifications. Therefore, the scope of the appended claims should be accorded the broadest interpretation so as to encompass all such modifications. For instance, three or five cutting marks can be formed during the manufacturing process by using another forming elements having three or five slots. In addition, the probe cover and the ring base can be engaged with each other.

What is claimed is:

1. A method for manufacturing a probe cover of a tympanic thermometer, comprising:

(a) forming an infrared transparent sheet;

(b) forming a sheath having a closed end and a circumferential peripheral flange, a plurality of unwanted parts being formed on an outer circumferential wall between the circumferential peripheral flange and the closed end of the sheath, and the closed end being formed into a flat window;

(c) hot-pressing the plurality of unwanted parts to form a plurality of fins; and (d) removing the plurality of fins to form a plurality of cutting marks.

2. The method for manufacturing the probe cover of the tympanic thermometer according to claim 1, further comprising:

(f) combining the circumferential peripheral flange of the probe cover with a ring base.

3. The method for manufacturing the probe cover of the tympanic thermometer according to claim 2, wherein the probe cover gradually decreases its cross-sectional area from the circumferential peripheral flange to the closed end.

4. The method for manufacturing the probe cover of the tympanic thermometer according to claim 2, wherein the step (b) is performed by using a forming member which includes a circumferential peripheral flange, a closed end opposite to the circumferential peripheral flange, and a plurality of slots on the outer circumferential wall between the circumferential peripheral flange and closed end, whereby the redundant material of the sheet is pressed out of the slots by pressing the sheet into the forming member at the circumferential peripheral flange.

5. The method for manufacturing the probe cover of the tympanic thermometer according to claim 1, further comprising:

(e) turning over the sheath to make the plurality of cutting marks located inside the sheath so that the outer circumferential wall thereof is smooth; and (f) combining the circumferential peripheral flange of the probe cover with a ring base.

6. A probe cover of a tympanic thermometer manufactured by the manufacturing method according to claim 2.

7. A probe cover of a tympanic thermometer manufactured by the manufacturing method according to claim 5.

* * * * *